(12) United States Patent
Trebbi

(10) Patent No.: US 7,042,231 B2
(45) Date of Patent: May 9, 2006

(54) METHOD FOR MONITORING THE PROPERTIES OF PHARMACEUTICAL ARTICLES

(75) Inventor: Roberto Trebbi, Castenaso (IT)

(73) Assignee: I.M.A. Industria Macchine Automatiche S.p.A., Bologna (IT)

( * ) Notice: Subject to any disclaimer, the term of this patent is extended or adjusted under 35 U.S.C. 154(b) by 0 days.

(21) Appl. No.: 10/487,938

(22) PCT Filed: Jun. 27, 2003

(86) PCT No.: PCT/IB03/02979

§ 371 (c)(1),
(2), (4) Date: Mar. 3, 2004

(87) PCT Pub. No.: WO2004/005903

PCT Pub. Date: Jan. 15, 2004

(65) Prior Publication Data

US 2004/0249591 A1   Dec. 9, 2004

(30) Foreign Application Priority Data

Jul. 4, 2002 (IT) ............................ BO2002A0432

(51) Int. Cl.
*G01N 22/00* (2006.01)
*G01N 27/00* (2006.01)

(52) U.S. Cl. ............... 324/639; 324/637; 324/71.1; 209/571; 73/866

(58) Field of Classification Search ........ 324/639–640; 209/592, 576, 645, 667, 571; 73/866
See application file for complete search history.

(56) References Cited

U.S. PATENT DOCUMENTS

| | | | | |
|---|---|---|---|---|
| 4,117,935 A | * | 10/1978 | Richardson et al. | 378/89 |
| 4,716,360 A | * | 12/1987 | Pakulis | 324/640 |
| 4,893,253 A | * | 1/1990 | Lodder | 702/28 |
| 5,515,740 A | | 5/1996 | Gamberini | |
| 5,682,733 A | * | 11/1997 | Perrone | 53/560 |
| 5,971,038 A | * | 10/1999 | Fiedler et al. | 73/866 |
| 6,111,415 A | * | 8/2000 | Moshe | 324/640 |
| 6,114,636 A | | 9/2000 | Cane', et al. | |
| 6,257,079 B1 | * | 7/2001 | Mueller | 73/866 |
| 6,316,946 B1 | | 11/2001 | Herrmann et al. | |
| 6,324,253 B1 | * | 11/2001 | Yuyama et al. | 378/57 |
| 6,383,553 B1 | | 5/2002 | Tondar et al. | |

FOREIGN PATENT DOCUMENTS

DE    33 36752 A1    4/1985

* cited by examiner

*Primary Examiner*—Diane Lee
*Assistant Examiner*—Marina Kramskaya
(74) *Attorney, Agent, or Firm*—Arent Fox PLLC

(57) ABSTRACT

In a method for monitoring the properties of pharmaceutical articles (2), in particular capsules (2), in a machine (1) that makes the articles (2), the pharmaceutical articles (2) are fed in single file from a station (3) where the articles (2) are made to an article (2) outfeed portion (6) of the machine (1) along a defined feed path (P) passing through an inspection station (8). In the inspection station (8) each pharmaceutical article (2) passes through an electromagnetic field (E) created by microwave radiation.

9 Claims, 2 Drawing Sheets

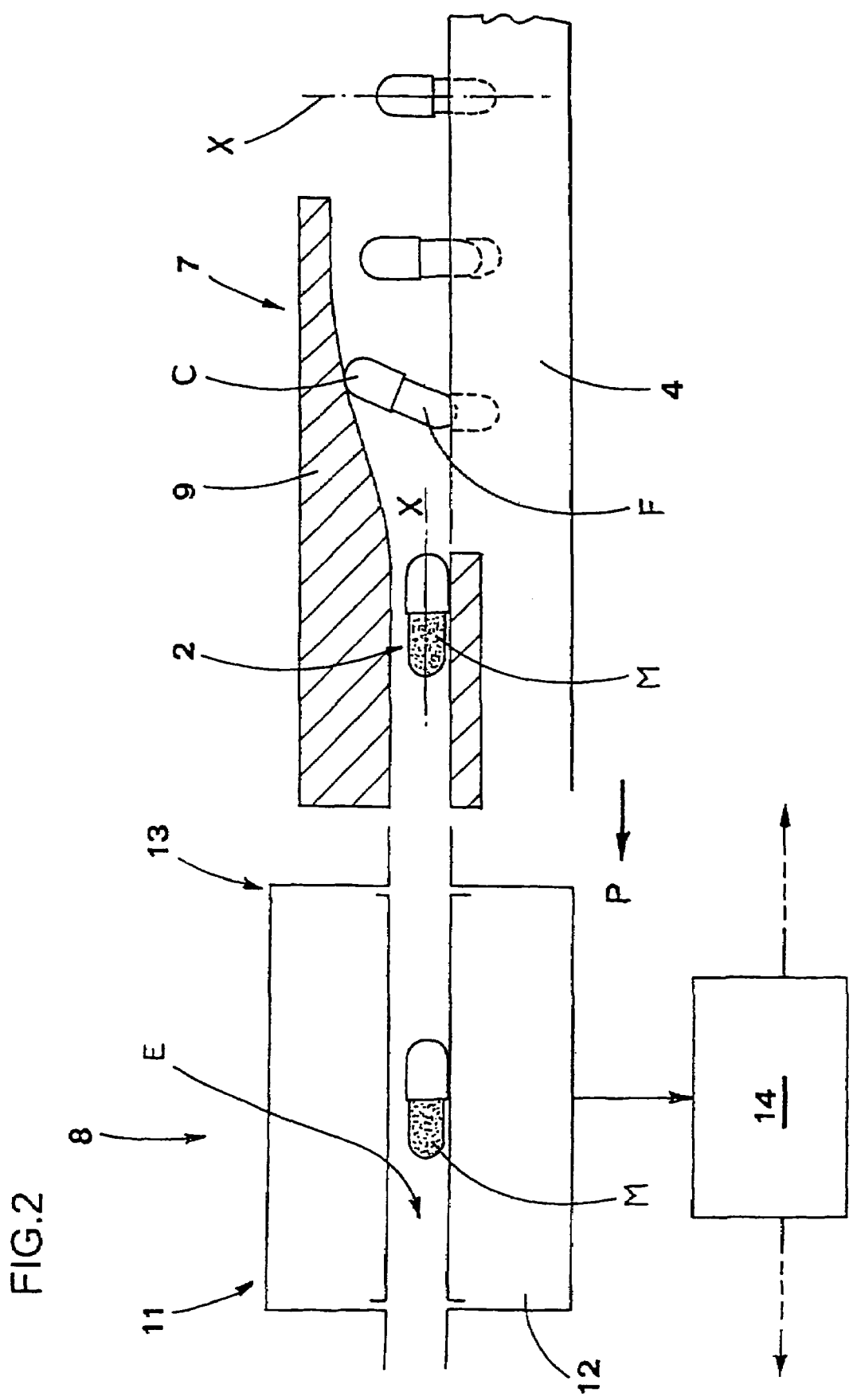

METHOD FOR MONITORING THE PROPERTIES OF PHARMACEUTICAL ARTICLES

CROSS-REFERENCE TO RELATED APPLICATION

This application is a National Stage entry of International Application No. PCT/IB2003/002979, filed Jun. 27, 2003, the entire specification claims and drawings of which are incorporated herewith by reference.

TECHNICAL FIELD

The present invention relates to a method for monitoring the properties of pharmaceutical articles.

In particular, the present invention can be advantageously applied to capsule filling machines for making hard gelatin capsules for pharmaceutical use, of the type with lid and body, which the present specification expressly refers to but without restricting the scope of the invention, in order to monitor defined chemico-physical properties, such as, the weight of the capsules and/or the density and/or moisture in the doses of pharmaceutical material inside the capsules.

BACKGROUND ART

In prior art capsule filling machines of the rotary turret type, currently used for filling capsules with doses of pharmaceutical material in powder or particulate form, the capsule weight is monitored in several ways, one of these being a statistical sampling method whereby defined quantities of sample capsules are taken at the outfeed end of the machine at defined time intervals and weighed on precision balances.

According to this method, which is manual and carried out outside the capsule filling machine, if a significant percentage of the sampled capsules are found to be unsatisfactory in terms of weight or do not fall within specified ranges of values, the operator in charge of testing operations must act directly on the capsule filling machine, modifying the dosing parameters of the unit that feeds and doses the pharmaceutical material.

In another method, known for example from European Patent EP 886765 B1, all the capsules made by the capsule filling machine, or a specified quantity of capsules, are fed into the hopper of a weighing apparatus located outside the capsule filing machine and connected to the capsule filing machine by suitable conveying means. This weighing apparatus comprises a rotating suction drum which is mounted under the hopper and which feeds the capsules in single file to a series of weighing heads followed by a conveyor chute with twin outfeed end.

The unit that controls the weighing apparatus receives and processes the signals from the weighing heads to derive the capsule weights and accordingly activates a deflection plate on the twin-outfeed chute so that unsatisfactory capsules are channelled into the outfeed portion of the chute connected to the reject container, while the satisfactory capsules are channelled into the other outfeed portion of the chute connected by suitable conveying means to a packaging machine downstream, for example, a blister packer. Even this apparatus, however, does not eliminate the need for manual operations. Thus, in this case too, if a significant percentage of the capsules are found to be unsatisfactory in terms of weight or do not fall within specified ranges of values, the operator must act directly on the capsule filling machine to adjust the dosing parameters of the system that feeds and doses the pharmaceutical material.

Besides the inconvenience of having to operate manually, outside the capsule filling machine to adjust the pharmaceutical material feeding and dosing system when significant percentages of the capsules are found to have an incorrect weight, there is also the disadvantage that the above mentioned prior art methods do not permit the measurement of other chemico-physical properties of the capsules, for example, the moisture content of the pharmaceutical material inside the capsules, which have a considerable influence on the weight of the capsules themselves.

DISCLOSURE OF THE INVENTION

The aim of the present invention is therefore to provide a method for monitoring the properties of pharmaceutical articles that overcomes the shortcomings and drawbacks of the prior art described above.

The invention accordingly provides a method for monitoring the properties of pharmaceutical articles in a machine that makes the articles, characterised in that the pharmaceutical articles are fed in single file from a station where the articles are made to an outfeed station of the articles themselves along a defined feed path passing through an inspection station; each pharmaceutical article passing through an electromagnetic field created by microwave radiation in the inspection station.

Preferably, crossing the electromagnetic field permits measurement of the weight of the pharmaceutical article.

DESCRIPTION OF THE DRAWINGS

The invention will now be described with reference to the accompanying drawings which illustrate a preferred, non-restricting embodiment of a unit, implementing the method according to the invention, for monitoring the properties of pharmaceutical articles, and in which:

FIG. 2 is a schematic front view of a detail of the unit of FIG. 1.

DETAILED DESCRIPTION OF THE PREFERRED EMBODIMENTS OF THE INVENTION

Figure 1:
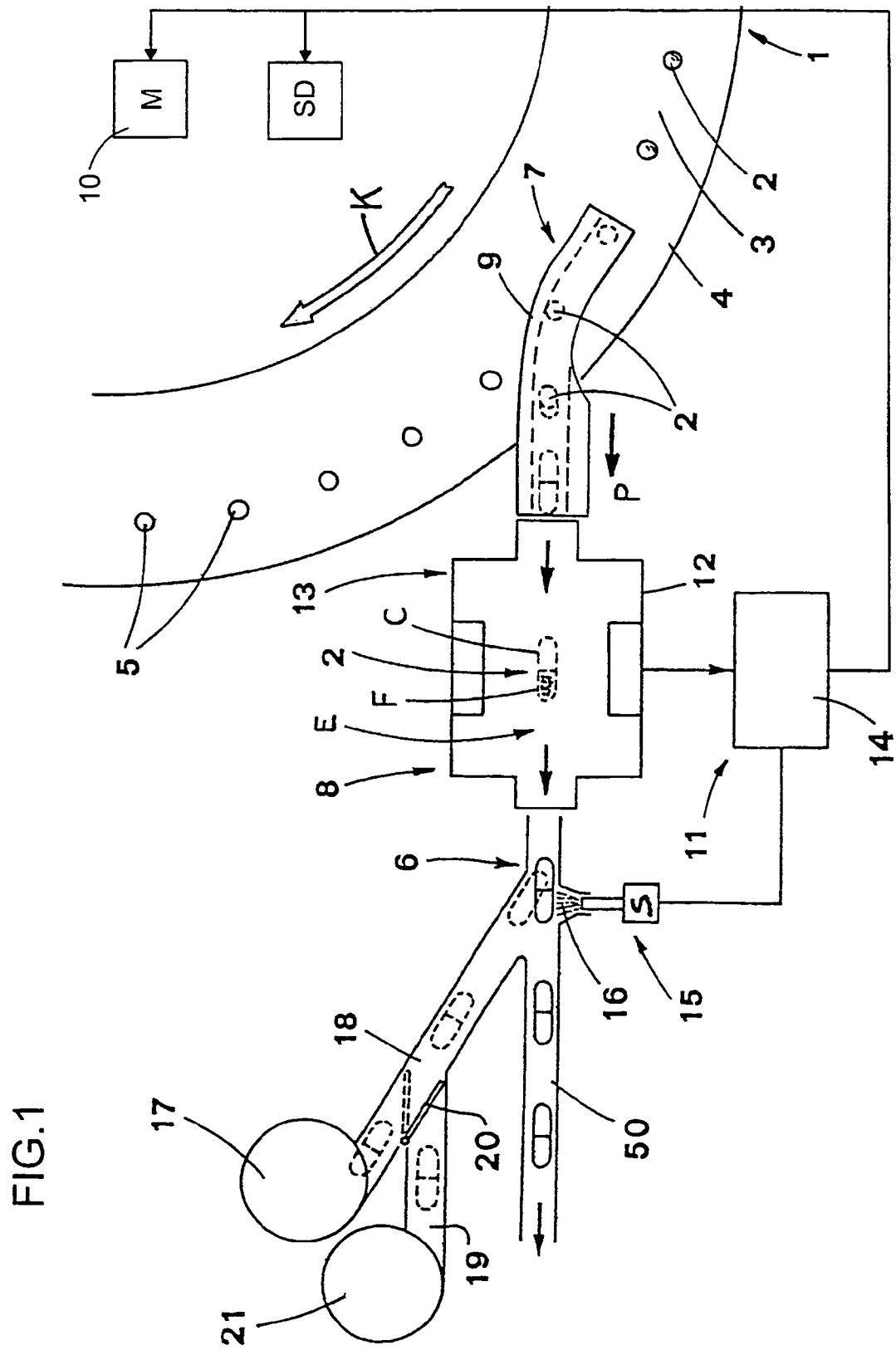
FIG. 1 is a schematic plan view, partly in cross section and with some parts cut away for clarity, of a preferred embodiment of the unit implementing the method according to the invention.

With reference to FIGS. 1 and 2, the numeral 1 denotes in its entirety a machine for filling hard gelatin capsules of known type, each having a lid C and a body F, with doses of pharmaceutical material M, in particular pharmaceutical material M in powder or particulate form, such as, for example, microtablets or pellets.

The capsule filling machine 1 is of well known type and basically comprises a station 3 for making the capsules 2, the station 3 in turn comprising a drum 4 that rotates, with alternating or continuous motion, in the direction indicated by the arrow K in FIG. 1, and being equipped on its periphery with a set of seats or bushes 5 for accommodating the capsules 2 once closed and filled with the material M. The material M is fed to the drum 4 in a known manner, which is not illustrated, through a central hopper 10 containing the material M which is dosed into the capsules 2 through a dosing system SD of the type, disclosed for example, in Italian Patent IT 1304779, with pistons that move inside respective cylindrical dosing chambers.

In the bushes 5 of the drum 4, each capsule 2 is set in a vertical position, that is to say, with longitudinal axis X (FIG. 2) positioned vertically and with the lid C at the top and the body F below.

From the drum 4, each capsule 2 is removed in succession from a respective bush 5, by customary expulsion means, which are not illustrated, and fed in single file to an outfeed portion 6 of the capsule filling machine 1 along a substantially straight feed path P by pneumatic conveying means which are of well known type and therefore not illustrated.

From the station 3 to the outfeed portion 6, the path P extends through a guide 7 and through a capsule 2 inspection station 8, and, downstream of the inspection station 8, the path P is defined by a channel 50 that leads in a known manner which is not illustrated into the infeed section of a packaging machine, for example a blister packer, also well known and not illustrated.

As shown in FIG. 2, the guide 7 is defined by a substantially helical contact element 9 designed to gradually tip each capsule 2 by 90°, so that it changes from an initially vertical orientation to a horizontal orientation where its lid C and body F lie flat on the drum 4 and where its longitudinal axis X is parallel to the horizontal plane defined by the drum 4 itself.

As illustrated in FIGS. 1 and 2, the inspection station 8 comprises an operating unit 11 which in turn comprises a microwave sensor 12 defined by a structure 13 inside which there is created a rotating electromagnetic field E of microwave radiation (that is to say, electromagnetic radiation with frequencies in the range from $10^{10}$ a $10^{12}$ Hertz) to which each capsule 2 is subjected as it moves along the path P and through the station 8.

More specifically, the microwave sensor 12 advantageously used is a sensor of known type, manufactured by the German company TEWS ELEKTRONIC, with an electric circuit surrounded by a thin layer of dielectric material, as described in U.S. Pat. No. 6,316,946 B2 and in United States Patent application US 2001/0015649 A1, both in the name of Manfred Tews.

Thus, as each capsule 2 passes through the inspection station 8, it crosses the electromagnetic field E generated by the microwave sensor 12 which tests some of its chemico-physical properties such as the density $\rho$ of the dose of material M with which each capsule 2 is filled, and the moisture content of the dose of the material M.

Since the volume of each capsule 2 is normally a known value and the value of the density of the material M is measured by the microwave sensor 12, the real weight W of each capsule 2 can be easily calculated from these values using the well known formula Weight W=(density $\rho$)× (Volume V).

The unit 11 also comprises a monitoring device 14 designed to receive as input a signal relating to the measured value of the weight of each capsule 2 moving through the structure 13 and/or to the moisture content of the material M in the capsule 2, to compare this measured value with a preset reference value, and to generate an output signal that activates a device 15 for rejecting any capsules 2 that do not conform with the reference value.

As illustrated in FIG. 2, the rejection device 15 comprises a nozzle 16 which is connected to a source S of air under pressure and which, on receiving a control signal from the monitoring device 14, issues a jet of air which diverts individual non-conforming capsules 2 from the path P, causing them to be expelled and fed out through a conveyor channel 18 leading into a rejection container 17.

The monitoring device 14 is also connected to the machine 1 system SD which doses the pharmaceutical material M so that, if a significant average percentage of the checked capsules 2 are found to be unsatisfactory, the device 14 sends a feedback signal to the dosing system SD in order to automatically adjust the material M dosing parameters of the machine 1.

During experiments conducted on the system described above, it was also found that the electromagnetic field E created by the microwave radiation and crossed by the capsules 2 can also be used to detect the presence in the material M of metal particles resulting from the treatment which the material M undergoes before entering the machine 1. Thus, the monitoring device 14 might also be advantageously used to activate the rejection device 15 to expel capsules 2 containing metal particles mixed with the material M.

In the embodiment illustrated in FIG. 1, the channel 18 also has a branch 19 with a deflector plate 20 which is controlled by the device 14 and which can connect the channel 18 to the branch 19 which leads into a container 21.

Thus, when a statistical check on a defined quantity of sample capsules 2 is required, the channel 18 is closed by the deflector plate 20 and the capsules 2 expelled by the jet of air from the nozzle 16 are diverted into the branch 19 which channels them into the container 21.

Advantageously, the sample capsules 2 collected in the container 21 can be weighed on analytical precision balances and the weights thus measured can be transferred to the memory medium of a personal computer together with the weights measured by the unit 11, so that the two sets of values can be compared and checked for significant deviations.

Thus, the unit 11 and the microwave sensor 12 can be periodically tested for working efficiency and, besides this, when deviations are found in a significant average number of samples, the system SD for dosing the material M in the capsule filling machine 1 can be adjusted accordingly.

To conclude, it is evident that the method as described above can be optimally applied to automatically measure and check within the machine 1 the weights of all the capsules 2 made by the machine 1 itself. Furthermore, the weights of only a specified quantity of sample capsules 2 can also be checked.

The invention claimed is:

1. A method for monitoring the properties of pharmaceutical articles in a machine that makes the articles, wherein the articles are fed in single file from a production station where the articles are made to an outfeed portion of the machine along a defined feed path passing through an inspection station; each article, while traveling through the inspection station, passes through an electromagnetic field created by microwave radiation, wherein a monitoring device is connected to a unit for feeding and dosing a pharmaceutical material contained in the articles in a capsule filling machine that makes the articles.

2. The method according to claim 1, wherein the crossing of the electromagnetic filed permits measurement of the weight of the article.

3. The method according to claim 1, wherein the articles comprise hard gelatin capsules having a lid and body containing doses of the pharmaceutical material in powder or particulate form; the crossing of the electromagnetic field permitting calculation of the weight of the articles through measurement of density (ρ) of the pharmaceutical material inside said each article.

4. The method according to claim 3, wherein the crossing of the electromagnetic field by the articles also permits measurement of a moisture content of the dose of pharmaceutical material inside said each article.

5. The method according to claim 3 or 4, wherein the crossing of the electromagnetic field by the articles also permits detection of any metal particles in the pharmaceutical material.

6. The method according to claim 4, wherein the electromagnetic field of microwave radiation is produced by an operating unit located inside the inspection station of the machine and which comprises a microwave sensor and the monitoring device; wherein the monitoring device is designed to receive as input a signal relating to a measured value of properties of the articles, compares the measured value with a preset reference value, and sends an output signal that activates a rejection device for rejecting the articles that do not conform with the reference value.

7. The method according to claim 6, the rejection device is located at the outfeed portion on the defined feed path and comprises deflecting means for diverting non-conforming articles from the defined feed path, causing the non-conforming articles to be expelled into a rejection container.

8. The method according to claim 7, wherein in the machine, the articles are fed from the production station to the outfeed portion along the defined feed path that passes through the inspection station and is substantially straight.

9. The method according to claim 8, wherein the articles are overturned as the articles move along the straight path upstream of the inspection station.

* * * * *